United States Patent
Priem et al.

(10) Patent No.: US 9,334,254 B2
(45) Date of Patent: *May 10, 2016

(54) PROCESS FOR PREPARING SULFONAMIDOBENZOFURAN DERIVATIVES

(75) Inventors: Thomas Priem, Paris (FR); Philippe Paul Vayron, Paris (FR)

(73) Assignee: SANOFI, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/638,500

(22) PCT Filed: Mar. 30, 2011

(86) PCT No.: PCT/FR2011/050707
§ 371 (c)(1),
(2), (4) Date: Sep. 28, 2012

(87) PCT Pub. No.: WO2011/124827
PCT Pub. Date: Oct. 13, 2011

(65) Prior Publication Data
US 2013/0023678 A1 Jan. 24, 2013

(30) Foreign Application Priority Data

Mar. 30, 2010 (EP) .................... 1052334

(51) Int. Cl.
*C07D 307/00* (2006.01)
*C07D 307/79* (2006.01)

(52) U.S. Cl.
CPC .................... *C07D 307/79* (2013.01)

(58) Field of Classification Search
None
See application file for complete search history.

(56) References Cited

U.S. PATENT DOCUMENTS

| | | | |
|---|---|---|---|
| 3,577,441 A | 5/1971 | Kaminsky et al. | |
| 3,657,350 A | 4/1972 | Mooradian et al. | |
| 3,937,737 A | 2/1976 | Eiglmeier | |
| 4,243,405 A | 1/1981 | Balasubramanyan et al. | |
| 4,666,931 A | 5/1987 | Ohishi et al. | |
| 5,066,803 A | 11/1991 | D'Ambra et al. | |
| 5,223,510 A | 6/1993 | Gubin et al. | |
| 6,555,697 B1 | 4/2003 | Schlama | |
| 6,828,448 B2 * | 12/2004 | Fino et al. ............ | 549/471 |
| 6,846,936 B2 | 1/2005 | Biard | |
| 6,855,842 B1 | 2/2005 | Schlama et al. | |
| 6,949,583 B2 | 9/2005 | Assens et al. | |
| 6,984,741 B2 | 1/2006 | Magerlein | |
| 7,148,240 B2 | 12/2006 | Assens et al. | |
| 7,312,345 B2 | 12/2007 | Gutman et al. | |
| 7,517,876 B2 | 4/2009 | Klein et al. | |
| 8,143,269 B2 | 3/2012 | Whitten et al. | |
| 8,501,971 B2 | 8/2013 | Friesz et al. | |
| 8,658,808 B2 | 2/2014 | Kretzschmar et al. | |
| 8,658,809 B2 | 2/2014 | Friesz et al. | |
| 8,674,121 B2 | 3/2014 | Kretzschmar et al. | |
| 8,686,180 B2 | 4/2014 | Bon et al. | |
| 8,748,636 B2 | 6/2014 | Bailly et al. | |
| 8,796,489 B2 | 8/2014 | Bailly et al. | |
| 8,816,103 B2 | 8/2014 | Friesz et al. | |
| 8,871,956 B2 * | 10/2014 | Bailly et al. ............ | 549/468 |
| 8,884,033 B2 | 11/2014 | Bon et al. | |
| 8,889,734 B2 | 11/2014 | Friesz et al. | |
| 8,962,869 B2 | 2/2015 | Grimaud et al. | |
| 2008/0033209 A1 | 2/2008 | Szarvas et al. | |
| 2010/0087415 A1 | 4/2010 | Whitten et al. | |
| 2010/0273764 A1 | 10/2010 | Andrews et al. | |

(Continued)

FOREIGN PATENT DOCUMENTS

| | | |
|---|---|---|
| CN | 101838252 A | 9/2010 |
| CN | 101993427 A | 3/2011 |

(Continued)

OTHER PUBLICATIONS

Sun, LQ. et al. N-{2-[2-(4-Phenylbutyl)benzofuran-4-yl]cyclopropylmethyl}-acetamide: an orally bioavailable melatonin receptor agonist. Bioorganic & Medicinal Chemistry Letters. 2004, vol. 14, p. 5159.*

Alcaraz, L. et al. Novel N-Aryl and N-Heteroaryl Sulfamide Synthesis via Palladium Cross Coupling. Organic Letters. 2004, vol. 6, p. 2706-2707, scheme 1 and Table 2.*

Sun, LQ. et al. N-{2-[2-(4-Phenylbutyl)benzofuran-4-yl]cyclopropylmethy1}-acetamide: an orally bioavailable melatonin receptor agonist. Bioorganic & Medicinal Chemistry Letters. 2004, vol. 14, p. 5159, scheme 3, compound 14.*

Cao, P. et al. Palladium-Catalyzed Intermolecular Coupling of Aryl Chlorides and Sulfonamides under Microwave Irradiation. Organic Letters. 2003, vol. 5, p. 4373.*

(Continued)

*Primary Examiner* — Rita Desai
*Assistant Examiner* — Ben S Michelson
(74) *Attorney, Agent, or Firm* — Morrison & Foerster LLP

(57) ABSTRACT

The invention relates to a process for preparing 5-sulfonamido-benzofuran derivatives of general formula: formula (I) in which R represents an alkyl or aryl group and $R_1$ and $R_2$ represent hydrogen or an alkyl or aryl group. According to the invention, the compounds of formula I are prepared by coupling a benzofuran derivative of general formula II, where X represents chlorine, bromine or iodine or a sulfonate group: formula (II) with a sulfonamide derivative of formula $R-SO_2-NH_2$, in the presence of a basic agent and of a catalyst system formed from a complex between a palladium compound and a ligand.

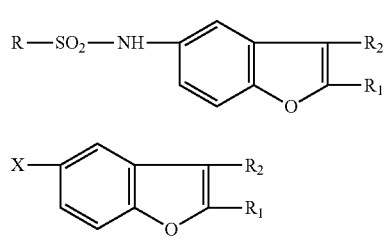

10 Claims, No Drawings

(56) References Cited

U.S. PATENT DOCUMENTS

| | | |
|---|---|---|
| 2013/0109868 A1 | 5/2013 | Friesz |
| 2014/0018553 A1 | 1/2014 | Grimaud et al. |
| 2014/0018554 A1 | 1/2014 | Friesz et al. |
| 2014/0081035 A1 | 3/2014 | Friesz et al. |
| 2014/0114081 A1 | 4/2014 | Friesz et al. |
| 2015/0005515 A1 | 1/2015 | Friesz et al. |
| 2015/0018568 A1 | 1/2015 | Friesz |
| 2015/0031901 A1 | 1/2015 | Bon et al. |
| 2015/0031902 A1 | 1/2015 | Huszar et al. |

FOREIGN PATENT DOCUMENTS

| | | |
|---|---|---|
| EP | 0 471 609 A1 | 2/1992 |
| EP | 0 735 083 A1 | 10/1996 |
| FR | 2 833 259 A1 | 6/2003 |
| WO | WO-96/05190 A1 | 2/1996 |
| WO | WO-02/48078 A1 | 6/2002 |
| WO | WO-02/48132 A1 | 6/2002 |
| WO | WO-03/040120 A1 | 5/2003 |
| WO | WO-03/048144 A2 | 6/2003 |
| WO | WO-03/048144 A3 | 6/2003 |
| WO | WO-2005/012301 A1 | 2/2005 |
| WO | WO-2007/022501 A2 | 2/2007 |
| WO | WO-2007/022501 A3 | 2/2007 |
| WO | WO-2007/100295 A1 | 9/2007 |
| WO | WO2007/133637 A2 | 11/2007 |
| WO | WO-2007/140989 A2 | 12/2007 |
| WO | WO-2007/140989 A3 | 12/2007 |
| WO | WO-2009/044143 A2 | 4/2009 |
| WO | WO-2009/044143 A3 | 4/2009 |
| WO | WO-2010/038029 A1 | 4/2010 |
| WO | WO-2010/040261 A1 | 4/2010 |
| WO | WO-2010/116140 A1 | 10/2010 |
| WO | WO-2010/136500 A1 | 12/2010 |
| WO | WO-2010/136502 A1 | 12/2010 |
| WO | WO-2011/070380 A1 | 6/2011 |
| WO | WO 2011/099010 * | 8/2011 |
| WO | WO 2011/099010 A1 * | 8/2011 |
| WO | WO-2011/104591 A1 | 9/2011 |
| WO | WO-2011/107705 A1 | 9/2011 |
| WO | WO-2011/158050 A1 | 12/2011 |
| WO | WO-2012/004658 A2 | 1/2012 |
| WO | WO-2012/004658 A3 | 1/2012 |
| WO | WO-2012/010788 A1 | 1/2012 |
| WO | WO-2012/010802 A1 | 1/2012 |
| WO | WO-2012/010913 A1 | 1/2012 |
| WO | WO-2012/032545 A1 | 3/2012 |
| WO | WO-2012/127173 A1 | 9/2012 |
| WO | WO-2012/131408 A1 | 10/2012 |
| WO | WO-2012/131409 A1 | 10/2012 |
| WO | WO-2012/131410 A1 | 10/2012 |
| WO | WO-2013/014478 A1 | 1/2013 |
| WO | WO-2013/014479 A1 | 1/2013 |
| WO | WO-2013/014480 A1 | 1/2013 |
| WO | WO-2013/121234 A1 | 8/2013 |
| WO | WO-2013/121235 A2 | 8/2013 |
| WO | WO-2013/121235 A3 | 8/2013 |
| WO | WO-2013/128294 A2 | 9/2013 |
| WO | WO-2013/128294 A3 | 9/2013 |
| WO | WO-2013/128294 A8 | 9/2013 |

OTHER PUBLICATIONS

Alcaraz, L. et al. Novel N-Aryl and N-Heteroaryl Sulfamide Synthesis via Palladium Cross Coupling. Organic Letters. 2004, vol. 6, p. 2706-2707.*

Kurti, L. et al. Strategic Applications of Named Reactions in Organic Synthesis. El Sevior. 2005, p. 448-449.*

Alcaraz, L. et al. Novel N-Aryl and N-Heteroaryl Sulfamide Synthesis via Palladium Cross Coupling. Organic Letters. 2004, vol. 6, p. 2706.*

Alcaraz, Lilian et al., "Novel N-Aryl and N-Heteroaryl Sulfamide Synthesis via Palladium Cross Coupling," Organic Letters (2004), vol. 6, No. 16, pp. 2705-2708.

Anjanappa, Prakash et al., "2-(Trimethylsilyl)ethanesulfonyl amide as a new ammonia equivalent for palladium-catalyzed amination of aryl halides," Tetrahedron Letters (2008), vol. 49, pp. 4585-4587.

Ikawa, Takashi et al., "Pd-Catalyzed Amidations of Aryl Chlorides Using Monodentate Biaryl Phosphine Ligands: A Kinetic, Computational, and Synthetic Investigation," Journal of the American Chemical Society (2007), vol. 129, pp. 13001-13007.

Yin, Jingjun et al., "Palladium-Catalyzed Intermolecular Coupling of Aryl Halides and Amides," Organic Letters (2000), vol. 2, No. 8, pp. 1101-1104.

Yin, Jingjun et al., "Pd-Catalyzed Intermolecular Amidation of Aryl Halides: The Discovery that Xantphos Can Be Trans-Chelating in a Palladium Complex," Journal of the American Chemical Society (2002), vol. 124, pp. 6043-6048.

Burton, George et al., "Palladium-Catalyzed Intermolecular Coupling of Aryl Chlorides and Sulfonamides Under Microwave Irradiation," Organic Letters (2003), vol. 5, No. 23, pp. 4373-4376.

International Search Report dated Jul. 8, 2011 issued in PCT/FR2011/050707.

Abramenko, et al., Polymethine Dyes—Furo[2,3-g] Benzothiazole Derivatives, Chemistry of Heterocyclic Compounds, vol. 11, (1975), pp. 1361-1364.

Adams, R. et al. Quinone imides. IV. P-Quinone monosulfonimides. Journal of the American Chemical Society. 1951, vol. 73, pp. 1145-1149.

Adams et al. (1956). "Quinone Imides. XXXIX. Adducts of Quinone Monoimides and Conversion of Active Methylene Adducts to Benzofurans," J. Am. Chem. Soc. 78(3):658-663.

Ando, M.E. et al. (1982). "Motion at the Active Site of Tosylchymotrypsin," Journal of the American Chemical Society 104(11):3172-3178.

Bartoli, G. et al. (1991). "Unexpected Elimination to α,β-Alkynylketones in the Reaction of Dianions of 1-Arylenaminones with Trimethylchlorosilane," Tetrahedron Letters 32(48):7091-7092.

Batra, S. et al. (2001). "Syntheses and Biological Evaluation of Alkanediamines as Antioxidant and Hypolipidemic Agents," Bioorganic & Medicinal Chemistry 9(12):3093-3099.

Bavin (1973). "2-Aminofluorene," Org. Syn. Coll. 5:30.

Berthold et al. (2002). "Transfer Hydrogenation in Ionic Liquids under Microwave Irradiation," Syn. 1607-1610.

Boovanahalli, Shanthaveerappa K. et al., "Application of Ionic Liquid Halide Nucleophilicity for the Cleavage of Ethers: A Green Protocol for the Regeneration of Phenols from Ethers," Journal of Organic Chemistry (2004), vol. 69, pp. 3340-3344.

Bourgery, et al., Synthesis and Antiarrhythmic Activity of New Benzofuran Derivatives, Journal of Medicinal Chemistry, (1981), vol. 24, No. 2, pp. 159-167.

Castellino, Angelo J. et al., "Synthesis of Benzofurans from Oxygenated Phenoxyamines," Journal of Organic Chemistry (1984), vol. 49, pp. 4399-4404.

Chauhan, Shive M.S. et al., "Microwave assisted dealkylation of alkyl aryl ethers in ionic liquids," Journal of Chemical Research (2004), p. 693-694.

Cheng, Lili et al., "Facile Cleavage of Ethers in Ionic Liquid," Bulletin of the Chemical Society of Japan (2007), vol. 80, No. 10, pp. 2008-2010.

Database PubChem Compound [Online] (Oct. 25, 2006),"CID 10095002—Compound Summary:N-[3-[4-(3-aminopropoxy)benzoyl)-2-butyl-1-benzofuran-5-yl", XP002676507, Database accession No. 15082344. Retrieved from the Internet: URL:http://pubchem.ncbi.nlm.nih.gov/summary/summary.cgi?sid=15082344&viewopt=PubChem [retrieved on May 23, 2012].

Delahay et al. (2007). "Past and Recent Approaches of Preparing Fe-ZSM-5," Current Topics in Catalysis 6:19-33.

Douglass, I.B. (1959). "Some New Reactions of Methanesulfenyl Chloride," Journal of Organic Chemistry 24:2004-2006.

Denmark, S.E. et al. (2008). "Lewis base catalysis in organic synthesis," Angew. Chem. Int. Ed. 47(9):1560-1638.

Fehnel, EA. (1958). "Quinoline Analogs of Podophyllotoxin. I. Preliminary Experiments. Syntheses of Some 4-Phenylquinoline Derivatives," J. Org. Chem. 23:432-434.

(56) References Cited

OTHER PUBLICATIONS

Fieser et al. (1967). "Reagents for Organic Synthesis," John Wiley & Sons, pp. 703-705.
Fontana (2008). "Syntheses of (R,S)-Naproxen and its 6-O-Desmethyiated metabolite labelled with 2H," *J. Labelled Compounds and Radiopharma.* 51:239-241.
Gilow, H.M. et al. (Jun.-Jul. 1991). "Sulfenylation of Some Pyrroles and Indoles," *J. Het. Chem.* 28:1025-1034.
Groves, J.K. (1972). "The Friedel—Crafts Acylation of Alkenes," Chem. Soc. Rev. 1:73-97.
Gutowski, Keith E. et al "Prediction of the Formation and Stabilities of Energetic Salts and Ionic Liquids Based on ab Initio Electronic Structure Calculations," The Journal of Physical Chemistry B (2005), vol. 109, pp. 23196-23208.
Haddadin et al. (1976). "Reaction to Benzofurazan Oxide with Unsymmetrical 1, 3-Diketones: Steric Polar Effects," *Tetrahedron* 32:719-724.
Hauser, CR. et al. (1948) "Alkaline cleavage of unsymmetrical β-diketones. Ring opening of acylcyclohexanones to form ε-acylcaproic acids," Journal of the American Chemical Society. 70:4023-4026.
Headley, Lindsay Sanders et al., "Dynamic Solvation in Imidazolium-Based Ionic Liquids on Short Time Scales," Journal of Physical Chemistry (2006), vol. 110, pp. 9549-9554.
Horton et al. (1967). "Reactions With Reactive Alkyl Halides," *J. Meth. In Enzymology* 11:556-565.
Imori et al. (2006). "Efficient Demethylation of N, N-Dimethylanilines with Phenyl Chloroformate in Ionic Liquids," *Synlett.* 16:2629-2632.
Johnson Matthey Handbook of Pharmaceutical Catalysis, 2009, pp. 1-106.
Joshi, KC. et al. (1986). "Some New Fluorinated β-Ketoamines and Their Copper Complexes," Synth. React. Inorg. Met. -Org. Chem. 1986, vol. 16(7):1009-1024.
Krongauz, ES. et al. Poly(anilophenylquinoxaline)s. Inst. Elementoorg. Soedin. 1986, vol. 28(4), p. 771 (Abstract).
Kwiatkowski, E. et al. (1978). Metal Benzoylpivaloylmethanates, Part I. Free Ligands and Copper(II) Chelates. Transition Met. Chem. 3:305-308.
Laszlo, Pierre et al., "Catalysis of Friedel-Crafts Alkylation by a Montmorillonite Doped with Transition-Metal Cations," Helvetica Chimica Acta (1987), vol. 70, pp. 577-586.
Liu, Tao et al., "Cleavage of Methyl Ethers of Flavones by Chloroaluminate Ionic Liquid," Synthetic Communications (2004), vol. 34, pp. 3209-3218.
Majdik (1985). "Studiul reactiei de ciclizare a orto-hidroxibenzilfenilcetonelor in benzofuran derivati," Revista de Chimie 36(8):760-761 (with English Translation).
Majdik et al. (1989). "Prepararea unor 2-(aril)-nitrobenzofurani din 0-(nitrofenil)-acetofenonoxime," Revista de Chemie, vol. 40, No. 8, pp. 689-693 (with English Translation).
Majdik et al. (1989). "0-Arilarea cetoximelor cu nitroclorbenzeni," Revista de Chemie, vol. 40, No. 6, pp. 490-493 (with English Translation).
March, J. (Jul. 1, 1992). "Aromatic Electrophilic Substitution," Chapter 11 in *Advanced Organic Chemistry, Reactions, Mechanism and Structure*, 4th edition, Wiley Interscience, pp. 538-542.
March, J. (Jul. 1, 1992). "Aliphatic Nucleophilic Substitution," Part 2 in *Advanced Organic Chemistry, Reactions, Mechanism and Structure*, 4th edition, Wiley Interscience, pp. 442.
Marvel, C.S. et al. (1941). "Diphenylacetic Acid," *Org. Synth. Coll.* vol. 1, 224-225.
Mehrotra, PK. et al. (2001). Search for new chemical entities as menses inducing agents. Contraception. 64:187-191.
Munch, R. et al. (1946). "The Preparation of Some α-Dialkylamino-ω-Methylaminoalkanes," *J. Am. Chem. Soc.* 68:1297-1299.

Nagy et al. (2007). "Isomorphous Substitution in Zeolites," *Mol. Sieves* 5:365-478.
Nakamura et al. (2004). "Pyrazole Derivatives as new potent and selective 20-hydroxy5,6,11,14-Eicosatetraenoic Acid Synthase Inhibitors," *Bioorganic Medic. Chem.* 12:6209-6219.
Pal, Santanu Kumar et al., "Synthesis of monohydroxy-functionalized triphenylene discotics: green chemistry approach," Tetrahedron (2007), vol. 63, pp. 6874-6878.
Roshchin, et al., Synthesis of Benzofurans via Pd2+-Catalyzed Oxidative Cyclization of 2-Allylphenols, Journal of Organometallic Chemistry. vol. 560, No. 1-2. (1998), pp. 163-167.
Sanfilippo, P.J. (1988). "Synthesis of (aryloxy)alkylamines. 1. Novel antisecretory agents with H+K+-ATPase inhibitory activity," *J. Med. Chem.* 31(9):1778-1785.
Serajuddin, ATM. (2007). "Salt formation to improve drug solubility," Advanced Drug Delivery Reviews 59:603-616.
Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," Indian Journal of Chemistry, vol. 208, pp. 234-237.
Skeels et al. (1989). "Zeolite Chemistry, Substitution of iron or titanium for Aluminum in Zeolites via reaction with the respective ammonium fluoride salts," *ACS Symposium series, zeolite Synthesis* 398:420-435.
Ślusarska, E. et al. (Feb. 1981). "One-Pot Phase-Transfer-Catalysed N-Alkylation of Diphenylphosphinamide with Alcohols in the Presence of Methanesulfonyl Chloride," *Synthesis* 155-156.
Son, J-K. et al. (1989). "Stereochemical Mechanism of Iodoacetic Acid Mediated Decomposition of $_L$-Methionine to $_L$-Homoserine Lactone," *Journal of the American Chemical Society* 111(4):1363-1367.
Tanaka, M. (1967). Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives, Bulletin of the Chemical Society of Japan 40(7):1724-1726.
Thornber, C. W. (1979). "Isosterism and molecular modification in drug design." Chem. Soc. Rev. 8:563-580.
Upthagrove, A.L. et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," *Drug Metab. Dispos.* 29(11):1377-1388.
Wamser, CC. et al. (1989). "Kinetics and Mechanisms for the Two-phase Reaction between Aqueous Aniline and Benzoyl Chloride in Chloroform, with and without Pyridine Catalysis," J. Org. Chem. 54:150-154.
Weissman, Steven A. et al., "Recent advances in ether dealkylation," Tetrahedron (2005), vol. 61, pp. 7833-7863.
Weitkamp et al. (1986). "Isomorphe Substitution in Zeolithen: Katalyse an Boro-, Alumo-und Galio-Silicaten mit ZSM-S-Strukter," *Chem. Ing. Tech.* 58(12):969-971 (with English Translation).
Wikipedia. (Nov. 5, 2012). "Reduction of Nitro Compounds."
Wu et al. (2004). "Immobilization of HX: [Hmim]X as Halogenating Agent, Recyclable Catalyst and Medium for Conversion of Alcohols to alkyl halides," *Chinese J. Chem.* 22:619-621.
Wuts, G.M., Greene's Protective Groups in Organic Synthesis, Fourth Edition, 2006, John Wiley and Sons, Chapter 7, Protection for the Amino Group, pp. 696-926.
Yang, H. et al. (2009). "Structure-based virtual screening for identification of novel 11 β-HSD1 inhibitors," European J. of Medicinal Chem. 44(3):1167-1171.
Zasshi, Y. (1956). "Studies on the Syntheses of Phenothiazine Derivatives. I. Syntheses of N-Substituted Phenothiazines by Tosylates," *J. Pharm. Soc. of Japan* 76:637-640 (with English Translation).
U.S. Appl. No. 14/377,484, filed Aug. 7, 2014, by Huszar et al.
U.S. Appl. No. 14/403,528, filed Nov. 24, 2014, by Huszar et al.

* cited by examiner

PROCESS FOR PREPARING SULFONAMIDOBENZOFURAN DERIVATIVES

The present invention relates generally to a process for preparing sulfonamidobenzofuran derivatives.

More specifically, the invention relates to a process for preparing 5-sulfonamidobenzofuran derivatives of general formula:

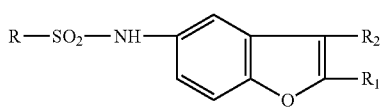

I in which R represents an alkyl or aryl group and $R_1$ and $R_2$, which may be identical or different, each represent hydrogen or an alkyl or aryl group.

In formula I above, R, $R_1$ or $R_2$ represents, in particular, a linear or branched $C_1$-$C_8$ alkyl group, especially a linear or branched $C_1$-$C_4$ alkyl group such as methyl, ethyl, n-propyl, isopropyl, n-butyl or tert-butyl or alternatively a substituted or unsubstituted phenyl group.

Among the group R, mention may be made of methyl, and among the group $R_1$, mention may be made of n-butyl.

In addition, in this formula I, among the group R, mention may be made of methyl, among the group $R_1$, mention may be made of n-butyl and among the group $R_2$, mention may be made of hydrogen.

Among the compounds of formula I above, 2-n-butyl-5-sulfoamidobenzofuran described in patent application WO 02/48132 has proven to be particularly useful as an intermediate product for the final preparation of amino-alkoxybenzoylbenzofuran derivatives, in particular for the preparation of 2-n-butyl-3-{4-[3-(di-n-butylamino)-propoxy]benzoyl}-5-methanesulfonamidobenzofuran, commonly known as dronedarone, and also pharmaceutically acceptable salts thereof. This methanesulfonamidobenzofuran derivative was described in patent EP 047 1 609, along with its therapeutic uses, especially in the cardiovascular field, where it proved to be particularly advantageous, for example, as an antiarryhythmic agent.

A process for synthesizing dronedarone was described in patent application WO 02/48132, mentioned previously, using 2-n-butyl-5-nitrobenzofuran, which is reduced, under pressure with hydrogen in the presence of platinum oxide as catalyst to form 2-n-butyl-5-aminobenzofuran. This benzofuran derivative is then subjected to the action of methanesulfonyl chloride, which gives 2-n-butyl-5-methanesulfonamidobenzofuran, which is treated with 4-[3-(di-n-butylamino)propoxy]benzoyl chloride to obtain dronedarone.

However, this process is not free of inherent drawbacks especially regarding the type of reaction used for the reagents used, namely hydrogenation under pressure, which entails an industrial risk, and also a treatment with methanesulfonyl chloride, a hazardous reagent which may generate genotoxic impurities (methanesulfonates).

The search for a process for preparing 2-n-butyl-5-methanesulfonamidobenzofuran that is capable of overcoming these drawbacks and disadvantages thus remains of fundamental interest.

It has now been found that it is possible to obtain this methanesulfonamidobenzofuran derivative, in good yield, by using reagents and reaction steps that are free of the drawbacks and disadvantages reported previously since it does not make use either of a catalytic hydrogenation reaction under pressure or of methanesulfonyl chloride.

According to the invention, the 5-sulfonamidobenzofuran derivatives of formula I may be prepared by coupling a benzofuran derivative of general formula:

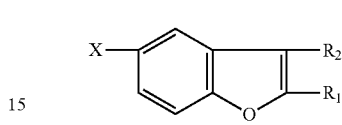

II in which $R_1$ and $R_2$ have the same meaning as previously and X represents chlorine, bromine or iodine or a sulfonate group of general formula:

III in which $R_3$ represents a trifluoromethane (—$CF_3$) or imidazolyl group, with a sulfonamide derivative of general formula:

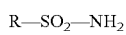

IV in which R has the same meaning as previously, in the presence of a basic agent and of a catalytic system formed from a complex between a palladium compound and a ligand, which gives the desired compounds.

The palladium complex used in the process of the invention is generally in the form of a palladium (0) compound, for instance:
tris(dibenzylideneacetone)dipalladium(0), referred to hereinbelow as $Pd_2(dba)_3$ or, advantageously,
bis(dibenzylideneacetone)palladium(0), referred to hereinbelow as $Pd(dba)_2$
and of a ligand generally chosen from phosphines, usually diarylphosphines.

These diarylphosphines are generally substituted in various ways. Thus, the aryl ring, such as phenyl, not bearing the phosphorus atom, may be mono- or especially polysubstituted, for example with an isopropyl group, while the aryl ring, especially phenyl, bearing the phosphorus atom, may in addition be mono- or polysubstituted. For example, this aryl ring does not comprise any substituents other than the phosphorus atom.

The phosphorus atom may itself be substituted, for example mono- or especially disubstituted, for example with alkyl or cycloalkyl groups such as tert-butyl or cyclohexyl.

By way of example, the following compounds may be used as ligands:
2-(di-tert-butylphosphino)-2',4',6'-triisopropyl-1,1'-biphenyl, referred to hereinbelow as ligand L1,
2-(dicyclohexylphosphino-2',4',6'-triisopropyl-1,1'-biphenyl, referred to hereinbelow as ligand L2,
2-(dicyclohexylphosphino)-2',6'-dimethoxy-1,1'-biphenyl, referred to hereinbelow as ligand L3,
2-(di-tert-butylphosphino)-3,4,5,6-tetramethyl-2',4',6'-triisopropyl-1,1'-biphenyl, referred to hereinbelow as ligand L4.

The ligand L1 is particularly advantageous.

The basic agent used in the process according to the invention may be chosen especially from alkoxides, but more generally from weaker bases such as phosphates or carbonates, for example alkali metal phosphates or alkali metal carbonates such as tripotassium phosphate, potassium carbonate or cesium carbonate.

In general, the coupling reaction is performed hot, for example at a temperature of between 60° C. and 120° C., and in a suitable solvent. This solvent may correspond to an alcohol, for instance tert-butanol, to an ether, for instance tetrahydrofuran or dioxane, or to a hydrocarbon, preferably an aromatic hydrocarbon, for instance toluene. However, dioxane is a solvent of choice in the context of the present invention.

The starting compounds of formula II may be prepared in various ways according to their chemical structure, as described hereinbelow.

A.—The compounds of formula II in which X represents chlorine, bromine or iodine may be obtained according to the following reaction scheme:

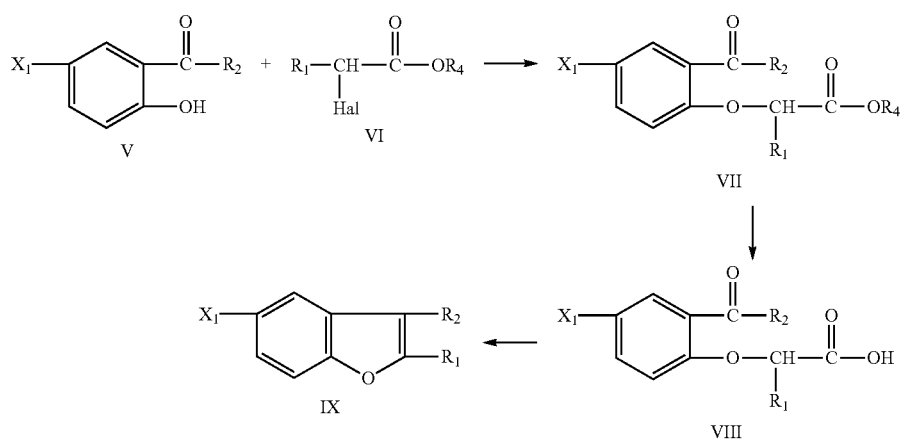

i.e. starting with a 2-hydroxyphenyl derivative of the formula V in which $R_2$ has the same meaning as previously and $X_1$ represents chlorine, bromine or iodine, which is reacted with a halo ester of formula VI in which $R_1$ has the same meaning as previously, Hal represents a halogen, preferably bromine, and $R_4$ represents a $C_1$-$C_4$ alkyl group, for instance ethyl, to form an ester of formula VII in which $R_1$, $R_2$, $R_4$ and $X_1$ have the same meaning as previously.

The reaction generally proceeds by heating in a suitable solvent, in particular a polar solvent such as N,N-dimethylformamide and in the presence of a basic agent such as an alkali metal carbonate.

The ester of formula VII is then saponified in a solvent, especially an ether, and in the presence of a suitable basic agent such as an alkali metal hydroxide, to form the corresponding salt of a carboxylic acid derivative, which is then treated with a strong acid, in a solvent such as an aromatic hydrocarbon, to give the carboxylic acid derivative of formula VIII in which $R_1$, $R_2$ and $X_1$ have the same meaning as previously.

In a subsequent step, the carboxylic acid derivative of formula VIII is then cyclized by heating in the presence of a benzenesulfonyl halide and of an acid acceptor such as a tertiary amine, the reaction generally proceeding by heating in a solvent such as an aromatic hydrocarbon, to give the compounds of formula IX in which $X_1$, $R_1$ and $R_2$ have the same meaning as previously, i.e. the desired compounds of formula II.

B.—The compounds of formula II in which X represents a sulfonate group may be obtained according to the following reaction scheme:

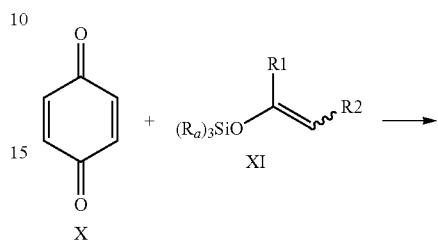

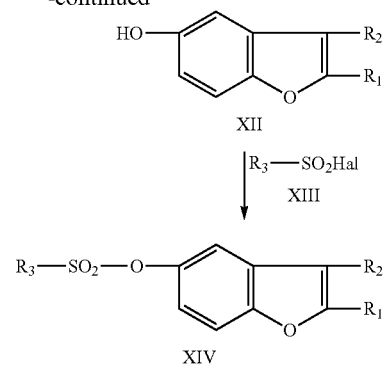

mainly starting with 1,4-benzoquinone of formula X, which is treated with a silyl enol ether of formula XI in which $R_1$ and $R_2$ have the same meaning as previously and $R_a$ represents a linear or branched $C_1$-$C_4$ alkyl group or a phenyl group, to form the 5-hydroxybenzofuran derivatives of formula XII in which $R_1$ and $R_2$ have the same meaning as previously.

The compound of formula XII is then coupled with a sulfonyl derivative of formula XIII in which Hal has the same meaning as previously, preferably chlorine, and $R_3$ has the same meaning as previously, in the presence of an acid acceptor, which gives the sulfonate derivatives of formula XIV in which $R_1$, $R_2$ and $R_3$ have the same meaning as previously, i.e. the desired compounds of formula II.

The benzofuran derivatives of general formula:

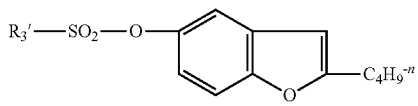

XV in which R'$_3$ represents a trifluoromethane or imidazolyl group, represent another subject of the present invention.

The non-limiting examples that follow illustrate the invention. In these examples, the abbreviations below are used:
TLC: thin-layer chromatography
HPLC: high-performance liquid chromatography
HPTLC: high-performance thin-layer chromatography
NMR: nuclear magnetic resonance
K$_3$PO$_4$: tripotassium phosphate
Cs$_2$CO$_3$: cesium carbonate
THF: tetrahydrofuran

PREPARATIONS

A. Ethyl 2-(4-bromo-2-formylphenoxy)hexanoate
(compound VII: R$_1$=n-C$_4$H$_9$; R$_2$=H; R$_4$=C$_2$H$_5$; X$_1$=Br)

8.9 g of potassium carbonate (64.3 mmol) and 45 ml of N,N-dimethylformamide are placed in an equipped reactor and then heated to 55° C. with stirring. A solution of 22 g of 2-hydroxy-5-bromobenzeneformaldehyde (compound V: X$_1$=Br) (107.2 mmol) in 40 ml of N,N-dimethylformamide is then poured in dropwise onto the mixture at 55° C., and the addition funnel is then rinsed with 10 ml of N,N-dimethylformamide. The medium is stirred at 55° C. for 30 minutes and then heated to 80° C. 20.8 ml of ethyl 2-bromohexanoate (compound VI: R$_1$=n-C$_4$H$_9$; R$_4$=C$_2$H$_5$; Hal=Br) (112.6 mmol) are added, and the addition funnel is rinsed with 10 ml of N,N-dimethylformamide. The reaction medium is maintained at 80° C. with stirring; the reaction progress is monitored by TLC (eluent: 7/1 methylcyclohexane/ethyl acetate; Rf of compound V: 0.53; Rf of compound VII: 0.44).

At the end of the reaction, the temperature of the reaction medium is cooled to 20° C., 100 ml of deionized water are then added slowly, leading to the demixing of an oil. This oil is decanted and separated from the aqueous phase, and then washed with 100 ml of water. After decantation and separation, the oil is diluted with 60 ml of toluene, and this organic phase is then washed again with 100 ml of deionized water. This last aqueous phase is back-extracted with 60 ml of ethyl acetate. The organic phases are combined and then concentrated on a rotary evaporator to give 34.9 g of the desired compound VII in the form of an orange-yellow oil.

Yield: 95%

$^1$H NMR (400 MHz, CDCl$_3$): δ 0.93 (t, J=7.4 Hz, 3H, —CH$_2$—CH$_2$—CH$_3$); 1.23 (t, J=7 Hz, 3H, —O—CH$_2$CH$_3$); 1.36-1.43 (m, 2H, —CH$_2$—CH$_2$—CH$_3$; 1.45-1.54 (m, 2H, —CH$_2$—CH$_2$—CH$_2$—); 1.99-2.05 (m, 2H, —CH$_2$—CH$_2$—CH—); 4.20 (q, J=7.2 Hz, 2H, —O—CH$_2$—CH$_3$; 4.71 (t, J=6 Hz, 1H, —CH$_2$—CH—O—); 6.71 (d, J=8.8 Hz, 1H, ArH); 7.56 (dd, J=9 and 2.6 Hz, 1H, ArH); 7.94 (d, J=2.4 Hz, 1H, ArH); 10.49 (s, 1H, CHO)

$^{13}$C NMR (CDCl$_3$): δ 188.3-170.6-159.3-138.1-131.1-126.9-115.2-114.5-77.4-61.6-32.3-27.3-22.3-14.2-13.9 ppm In the same manner, but starting with 10 g or 50 g of compound V, the desired compound VII was obtained in yields of 98% and 94%, respectively.

B. 2-(4-Bromo-2-formylphenoxy)hexanoic acid
(Compound VIII: R$_1$=n-C$_4$H$_9$; R$_2$=H; X$_1$=Br)

60 g of ethyl 2-(4-bromo-2-formylphenoxy)hexanoate (compound VII) (0.17 mmol) and 52 ml of methyl tert-butyl ether are placed in an equipped reactor. 78 ml of deionized water and a solution of 9.37 g of 23% sodium hydroxide (0.23 mmol) in 31.4 g of deionized water are added, at 20° C. The reaction medium is heated to 40° C. with stirring and the saponification of the ester is monitored by TLC (eluent: 8/2 methylcyclohexane/ethyl acetate+a few drops of acetic acid; Rf of the compound VII=0.52; Rf of compound VIII=0.08).

At the end of the reaction, the temperature of the reaction medium is returned to 20° C. and 25.5 g of sodium chloride (0.43 mol) in 130 ml of deionized water are added, followed by 270 ml of toluene. With stirring, the reaction medium is acidified by slow addition of 20 ml of 37% hydrochloric acid solution, without exceeding 25° C. The two phases are decanted and separated, and the organic phase is then washed with 80 ml of deionized water. After separation of the phases, the organic phase is concentrated under vacuum on a rotary evaporator to give 54.7 g of a red oil, which crystallizes when cold.

After reslurrying in a diisopropyl ether/heptane mixture, 45.5 g of the desired compound VIII are isolated in the form of a yellow-white solid.

Yield: 82%

$^1$H NMR (400 MHz, CDCl$_3$): δ 0.93 (t, J=7.2 Hz, 3H, —CH$_2$—CH$_2$—CH$_3$); 1.37-1.44 (m, 2H, —CH$_2$—CH$_2$—CH$_3$); 1.49-1.57 (m, 2H, —CH$_2$—CH$_2$—CH$_2$—); 2.05-2.11 (m, 2H, —CH$_2$—CH$_2$—CH—); 4.79 (t, J=6 Hz, 1H, —CH$_2$—CH—CO—); 6.78 (d, J=8.8 Hz, 1H, ArH); 7.61 (dd, J=8.8 and 2.4 Hz, 1H, ArH); 7.94 (d, J=2.4 Hz, 1H, ArH); 10.39 (s, 1H, CHO)

$^{13}$C NMR (CDCl$_3$): δ 188.6-174.3-158.6-138.3-132.4-127.0-115.5-114.9-77.2-32.2-27.1-22.3-13.8 ppm C. 2-n-Butyl-5-bromobenzofuran (compound IX: R$_1$=n-C$_4$—H$_9$; R$_2$=H; X$_1$=Br)

25.8 ml of benzenesulfonyl chloride (0.202 mol; 1.4 equivalents) and 40 ml of toluene are placed in an equipped reactor and the mixture is stirred at 80° C. 65 ml of anhydrous triethylamine (0.47 mol) and then 45.2 g of 2-(4-bromo-2-formylphenoxy)hexanoic acid (compound VIII) (0.144 mol) dissolved in 250 ml of toluene are then added slowly at 80° C. The reaction progress is monitored by TLC (eluent: 80/20 methylcyclohexane/ethyl acetate; Rf of compound VIII=0.08; Rf of the desired compound IX=0.80).

At the end of the reaction, the temperature of the reaction medium is returned to 20° C. The excess benenesulfonyl chloride is destroyed by addition of 250 ml of aqueous 5% sodium hydroxide solution. The phases are decanted and separated and the organic phase is then washed with a mixture of 70 ml of deionized water and 6.8 ml of 37% hydrochloric acid. The phases are decanted and separated and the organic phase is then washed with 75 ml of deionized water. The organic phase is washed with a solution of 7.73 g of sodium hydroxide dissolved in 67 ml of deionized water. The phases are decanted and separated and the organic phase is then washed with a solution of 7.53 g of sodium chloride in 70 ml of deionized water. The pH of the aqueous phase is adjusted to between 5 and 8 with 7% hydrochloric acid solution. The phases are decanted and separated and the organic phase is then concentrated on a rotary evaporator to give 37.2 g of a brown oil.

This oil is purified by chromatography on silica gel (eluent: 80/20 methylcyclohexane/ethyl acetate) to give 24.3 g of the desired compound IX in the form of a yellow oil.

Yield: 67%

$^1$H NMR (400 MHz, DMSO-d6): δ 0.91 (t, J=7.2 Hz, 3H, —CH$_2$—CH$_2$—CH$_3$); 1.30-1.40 (m, 2H, —CH$_2$—CH$_2$—CH$_3$); 1.61-1.69 (m, 2H, —CH$_2$—CH$_2$—CH$_2$—); 2.76 (t, J=7.4 Hz, 2H, —CH$_2$—CH$_2$-Cq); 6.57 (s, 1H, ArH); 7.33 (dd, J=8.8 and 2 Hz, 1H, ArH); 7.46 (d, J=8.8 Hz, 1H, ArH); 7.72 (dd, 2 Hz, 1H, ArH)

EXAMPLES 1 TO 5

2-n-Butyl-5-methanesulfonamidobenzofuran
(compound I: R═CH$_3$; R$_1$═n-C$_4$H$_9$, R$_2$═H)

The following are placed in a 20 ml tube predried in an oven: 2 equivalents of base and 1.5 equivalents of methanesulfonamide, 2 mol % of Pd(dba)$_2$ and 5 mol % of 2-(di-tert-butylphosphino)-2',4',6'-triisopropyl-1,1'-biphenyl (ligand L1). The tube is stoppered with a septum and placed under an inert atmosphere of argon, and 1 equivalent of 2-n-butyl-5-bromobenzofuran (compound IX or II) dissolved in 10 volumes of solvent is then added by syringe. The reaction medium is then stirred and heated to the reflux point of the solvent or at 100° C. for 24 hours, while monitoring the reaction progress by TLC (eluent: 20/80 ethyl acetate/methylcyclohexane) or by HPLC. At the end of the reaction, the reaction medium is diluted with ethyl acetate and then filtered while hot. The filtrate is then concentrated to give, when cold, crystallization of the desired compound I.

The following results were obtained:

| Example | Base | Solvent | Yield (%) |
| --- | --- | --- | --- |
| 1 | K$_3$PO$_4$ | tert-butanol | 45 |
| 2 | Cs$_2$CO$_3$ | dioxane | 100 |
| 3 | Cs$_2$CO$_3$ | THF | 50 |
| 4 | Cs$_2$CO$_3$ | toluene | 60 |
| 5 | K$_3$PO$_4$ | dioxane | 81 |

EXAMPLE 6

2-n-Butyl-5-methanesulfonamidobenzofuran
(compound I: R═CH$_3$; R$_1$═n-C$_4$H$_9$, R$_2$═H)

The following are placed in an equipped reactor under an argon atmosphere: 13 g of cesium carbonate (39.9 mmol), 3 g of methanesulfonamide (31.5 mmol), 250 mg of Pd(dba)$_2$ (0.4 mmol) and 440 mg of 2-(di-tert-butylphosphino)-2',4',6'-triisopropyl-1,1'-biphenyl (ligand L1) (1.04 mmol). 5.5 g of 2-n-butyl-5-bromobenzofuran (compound IX or II) (21.7 mmol) dissolved in 55 ml of dioxane are then added by syringe. The reaction medium is then stirred and heated at 100° C. for 24 hours.

The reaction medium is then diluted with 40 ml of ethyl acetate and the first crystallization crop is filtered off on a Buchner funnel. After isolation of a second crop, 3.6 g of the desired compound I are isolated in the form of a snow-white powder.

Yield: 68%

$^1$H NMR (400 MHz, DMSO-d6): δ 0.91 (t, J=7.4 Hz, 3H, —CH$_2$—CH$_2$—CH$_3$); 1.31-1.40 (m, 2H, —CH$_2$—CH$_2$—CH$_3$); 1.59-1.66 (m, 2H, —CH$_2$—CH$_2$—CH$_2$—); 2.47 (s, 3H, CH$_3$—SO$_2$—); 2.66 (t, J=7.4 Hz, 2H, —CH$_2$—CH$_2$-Cq-); 6.27 (s, 1H, ArH); 6.61 (dd, J=8.8 and 2 Hz, 1H, ArH); 6.94 (d, J=2 Hz, 1H, ArH); 7.02 (dd, J=8.8 Hz, 1H, ArH)

$^{13}$C NMR (DMSO-d6); δ 157.6-147.2-147.0-128.6-117.9-109.4-108.8-101.8-38.3-29.3-27.4-21.6-13.6 ppm

The invention claimed is:
1. A process for preparing 5-sulfonamidobenzofuran derivatives of general formula:

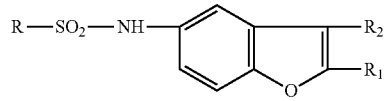

in which R represents an alkyl or aryl group and R$_1$ and R$_2$, which may be identical or different, each represent hydrogen or an alkyl or aryl group, comprising coupling a benzofuran derivative of general formula:

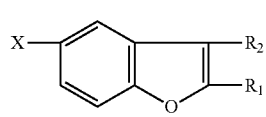

in which R$_1$ and R$_2$ have the same meaning as previously and X represents chlorine, bromine or iodine or a sulfonate group of general formula:

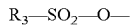

in which R$_3$ represents a trifluoromethane or imidazolyl group, with a sulfonamide derivative of general formula:

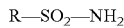

in which R has the same meaning as previously, in the presence of a basic agent and of a catalytic system formed from a complex between a palladium compound and a ligand wherein the palladium compound is selected from the group consisting of bis(dibenzylideneacetone)palladium(0) and tris(dibenzylideneacetone)dipalladium (0), and wherein the ligand is 2-(di-tert-butylphosphino)-2',4',6'-triisopropyl-1,1'-biphenyl.

2. The process as claimed in claim 1, wherein R, R$_1$ or R$_2$ represents a linear or branched C$_1$-C$_8$ alkyl group or a substituted or unsubstituted phenyl group.

3. The process as claimed in claim 1, wherein R, R$_1$ or R$_2$ represents a linear or branched C$_1$-C$_4$ alkyl group.

4. The process as claimed in claim 1, wherein R represents methyl, R$_1$ represents n-butyl and R$_2$ represents hydrogen.

5. The process as claimed in claim 1, wherein the basic agent is an alkali metal phosphate or an alkali metal carbonate.

6. The process as claimed in claim 5, wherein the basic agent is tripotassium phosphate, potassium carbonate or cesium carbonate.

7. The process as claimed in claim 1, wherein the coupling is performed at a temperature of between 60° C. and 120° C.

8. The process as claimed in claim 1, wherein the coupling is performed in a solvent chosen from an alcohol, an ether and an aromatic hydrocarbon.

9. The process as claimed in claim 8, wherein the solvent is dioxane.

10. The process as claimed in claim 1 wherein $R_2$ is selected from methyl, ethyl, n-propyl, isopropyl, n-butyl, or tert-butyl.

\* \* \* \* \*